United States Patent
Frondoza et al.

(10) Patent No.: US 9,421,234 B2
(45) Date of Patent: Aug. 23, 2016

(54) ORALLY ADMINISTRABLE COMPOSITIONS COMPRISING AVOCADO/SOYBEAN UNSAPONIFIABLES AND LIPOIC ACID AND METHODS OF ADMINISTRATION

(75) Inventors: Carmelita Frondoza, Woodstock, MD (US); Todd R. Henderson, Charlotte, NC (US); Reinhard Grzanna, Woodstock, MD (US)

(73) Assignee: NUTRAMAX LABORATORIES, INC., Edgewood, MD (US)

( * ) Notice: Subject to any disclaimer, the term of this patent is extended or adjusted under 35 U.S.C. 154(b) by 0 days.

(21) Appl. No.: 13/112,488

(22) Filed: May 20, 2011

(65) Prior Publication Data

US 2012/0294960 A1    Nov. 22, 2012

(51) Int. Cl.
*A61K 36/54* (2006.01)
*A61K 31/385* (2006.01)
*A61K 36/48* (2006.01)

(52) U.S. Cl.
CPC .............. *A61K 36/54* (2013.01); *A61K 31/385* (2013.01); *A61K 36/48* (2013.01)

(58) Field of Classification Search
None
See application file for complete search history.

(56) References Cited

U.S. PATENT DOCUMENTS 6,355,280 B1 * 3/2002 Segal et al. ............... 424/757
7,288,278 B2 * 10/2007 Mellerup et al. ......... 426/606
2010/0035816 A1   2/2010 Piccirilli et al.

FOREIGN PATENT DOCUMENTS

WO    WO 2009123597 A1 * 10/2009
WO    WO 2010078324 A2 *  7/2010
WO    WO2011/018501 A2    2/2011

OTHER PUBLICATIONS

Matsugo et al. Biochemical and Biophysical Research Communications 240, 819-824 (1997).*
Boilou et al. Arthritis Research & Therapy 2009, 11:R41. pp. 1-9.*
Koufaki et al. "Design and synthesis of 1,2-dithiolane derivatives and evaluation of their neuroprotective activity," Bioorg. Med. Chem. Lett. 17(2007): 4223-4227.

* cited by examiner

*Primary Examiner* — Amy L Clark
(74) *Attorney, Agent, or Firm* — King & Schickli, PLLC

(57) ABSTRACT

Methods comprising administration of: (i) avocado/soybean unsaponifiables and (ii) lipoic acid or derivatives thereof, to a mammalian or an avian subject are provided. This invention also relates to orally administrable compositions comprising avocado/soybean unsaponifiables and lipoic acid or derivatives thereof.

1 Claim, 2 Drawing Sheets

FIGURE 1: Effect of ASU and Lipoic Acid (LA) on $PGE_2$ production in LPS (10 ng/ml) activated equine chondrocyte cultures.
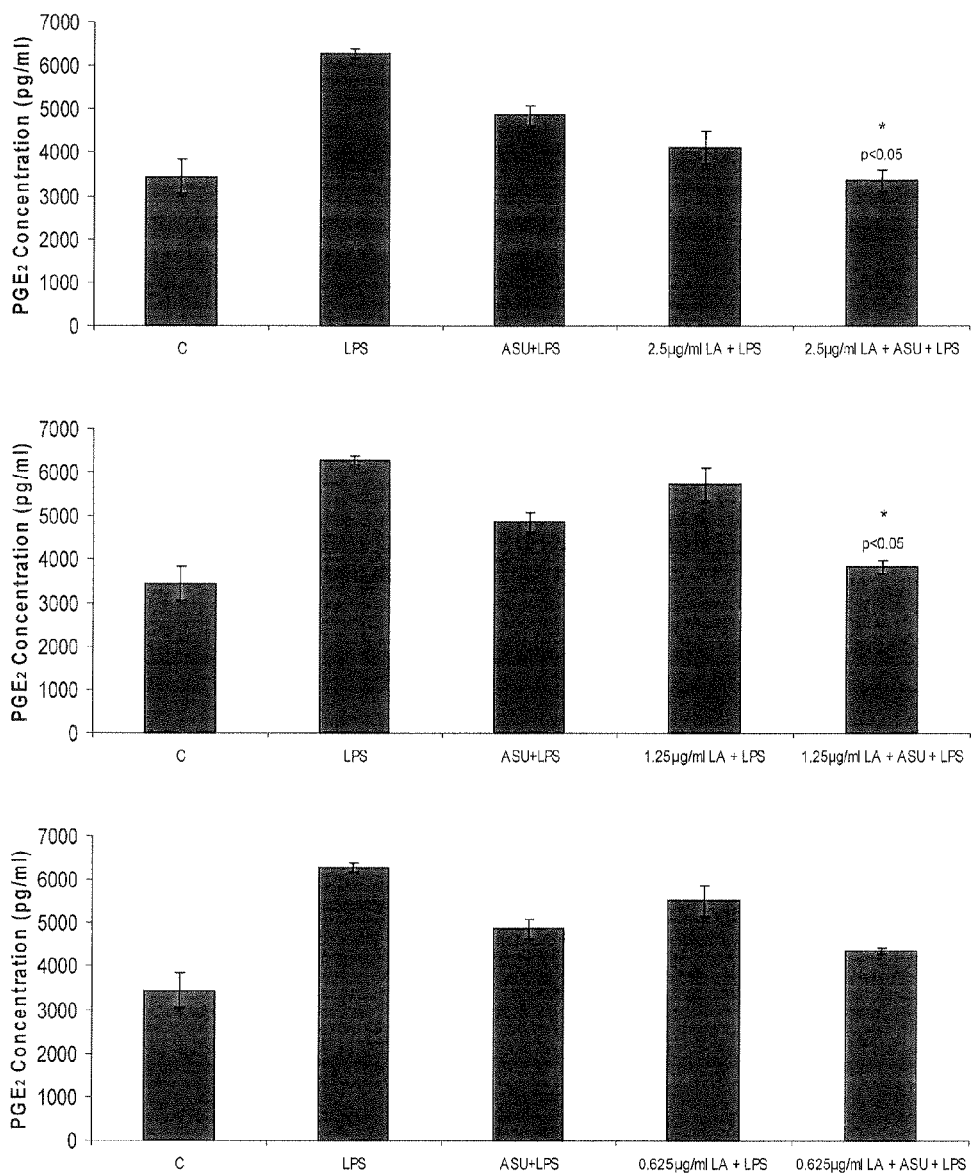

FIGURE 2: Effect of ASU and Lipoic Acid (LA) on $PGE_2$ production in $H_2O_2$ activated equine chondrocyte cultures.
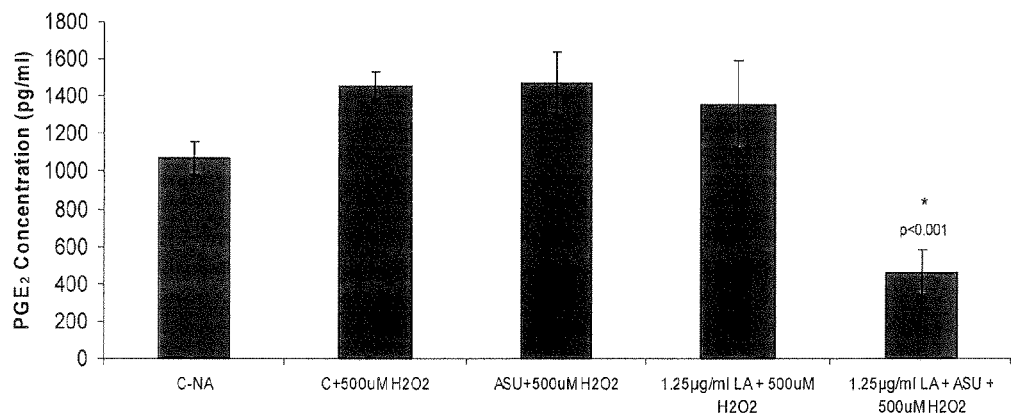
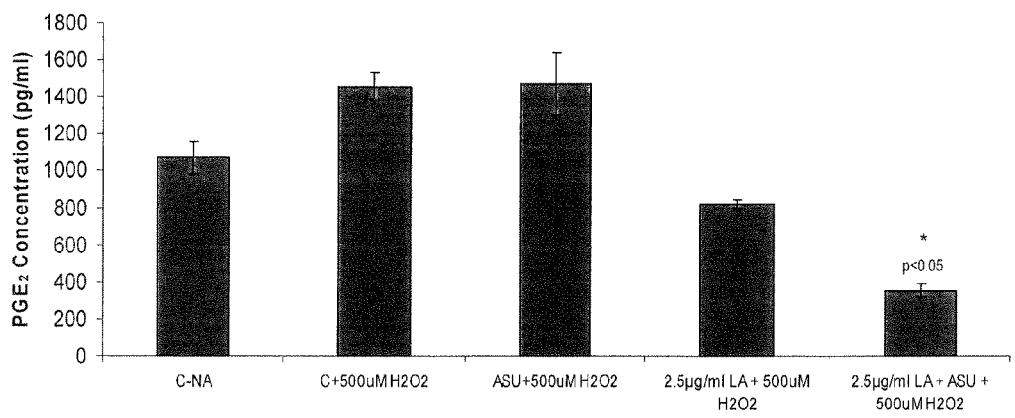

ORALLY ADMINISTRABLE COMPOSITIONS COMPRISING AVOCADO/SOYBEAN UNSAPONIFIABLES AND LIPOIC ACID AND METHODS OF ADMINISTRATION

FIELD OF THE INVENTION

The present invention provides methods comprising administration of: (i) avocado/soybean unsaponifiables and (ii) lipoic acid or derivatives thereof, to a mammalian or an avian subject. The present invention also provides orally administrable compositions comprising avocado/soybean unsaponifiables and lipoic acid or derivatives thereof.

BACKGROUND OF THE INVENTION

Connective tissue is the structural framework of cartilage, bone, synovium, ligament, meniscus, and tendon in articulating joints. Components of connective tissue are produced by resident cells and then secreted to form the extracellular matrix (ECM) characteristics of the tissue. In addition to serving as structural framework, the ECM also plays a critical role in cell communication and function. In articular cartilage, chondrocytes are aligned in a distinct pattern within the type II collagen ECM framework. Bone forming osteoblasts and osteocytes, as well as bone resorbing osteoclasts, are organized in mineralized type I collagen ECM. The few fibroblast-like and macrophage-like cells in the synovium are also held in place by ECM. Similarly, tenocytes and ligament cells are assembled together within the ECM. The synthesis and breakdown of connective tissue ECM is controlled by a network of regulatory molecules which are also produced by the resident tissue cells. This network includes growth factors and a wide array of molecules known as pro-inflammatory mediators. They include cytokines, chemokines, prostaglandins and nitric oxide. These molecules exhibit many biological activities. They can induce cell proliferation or cell death. These substances can also induce anabolic pathways for production of ECM or induce catabolic enzymes that can break down the ECM, Under physiological conditions, cell survival or death, the production or breakdown of connective tissue ECM is tightly controlled to maintain balanced homeostasis. The production and function of regulatory molecules is modulated by many factors including mechanical forces, physical factors such as temperature and pH, chemicals, microbes and their products. Under certain conditions, these factors can elicit excessive and untimely production of regulatory molecules leading to irreparable tissue damage, loss of function and death.

Inflammation and Pro-Inflammatory Mediators

Tissues react to mechanical, physical, chemical insults and infection by an inflammatory response. The inflammation process is known to lead to recovery, to healing, defense against infection and is usually life preserving. The inflammatory response in humans and animals consists of two phases. The initial phase is characterized by the local synthesis of pro-inflammatory mediators such prostaglandins and leukotrienes. They are derived from arachidonic acid through the action of cyclooxygenases and lipoxygenases. These pro-inflammatory mediators increase local blood flow and enhance the permeability of endothelial cells to allow leukocyte recruitment and accumulation. Other pro-inflammatory mediators which are subsequently produced include cytokines (IL-1β, TNF-α), chemokines (IL-8), and nitric oxide. In the second phase, the resolution phase, prostaglandins generated during the initial phase activate enzymatic pathways along which arachidonic acid is converted to chemical mediators with anti-inflammatory properties. It has been reported that prostaglandin $E_2$ ($PGE_2$) activates the expression of 15-lipoxygenase which generates anti-inflammatory lipoxins from arachidonic acid. Thus, the resolution of inflammation is driven by the pro-inflammatory response. These studies indicate that the initiation, progression and termination of the inflammation process are tightly controlled. Prolonged, exaggerated inflammation has been associated with many disorders including osteoarthritis (OA), rheumatoid arthritis (RA), Alzheimer's disease and cardiovascular disease.

In joint tissues, chondrocytes, synoviocytes, osteoblasts, osteoclasts, ligament cells, and tenocytes produce a wide array of pro-inflammatory mediators. Among these is prostaglandin $E_2$ ($PGE_2$), which is known to play a regulatory role by inducing the production of other mediators including cytokines, nitric oxide, and connective tissue degrading metalloproteinase (MMP) enzymes. Due to its ability to induce metalloproteinases (MMPs), $PGE_2$ contributes to the breakdown of cartilage ECM. In addition, $PGE_2$ promotes bone resorption and osteophyte formation. $PGE_2$ sensitizes nociceptors on peripheral nerve endings, thereby contributing to the development of inflammatory pain. $PGE_2$ levels are locally regulated by the inducible cyclooxygenase-2 (COX-2) enzyme, a nitric oxide synthase in chondrocytes that inhibits cartilage and proteoglycan degradation. In pathologic conditions such as osteoarthritis, COX-2 expression is up-regulated with a concomitant increase in $PGE_2$ production.

The role of other tissues in the inflammation process is also well established. Inflammation of the synovial membrane is now recognized to be a key event in cartilage degradation in osteoarthritis, particularly during the early stages of the disease. Synovitis is characterized by activation of resident macrophage-like cells and fibroblast-like cells in the synovial membrane which leads to production of excessive amounts of pro-inflammatory mediators including TNF-α, IL-1β and $PGE_2$, Recent evidence suggests that synovial macrophages are the main source of the cytokines in the earliest stages of osteoarthritis and that they are important contributors to the cartilage damage in osteoarthritis throughout the course of the disease. Cytokines also induce production of $PGE_2$ and active metalloproteinases (MMPs). It is now well accepted that these mediators control the balance between ECM destruction and repair, which has made these molecules preferred targets for therapeutic intervention. Other tissues in the joint such as the subchondral bone also produce pro-inflammatory mediators that modulate joint health.

In addition to pro-inflammatory mediators such as cytokines and prostaglandins, reactive oxygen species (ROS) have also been implicated in joint degeneration observed in osteoarthritis. Oxidative stress induced by ROS such as nitric oxide and hydrogen peroxide has been shown to cause chondrocyte apoptosis and cartilage ECM breakdown. Moreover, ROS have been reported to activate signal transduction pathways that lead to an increased production of pro-inflammatory mediators including cytokines and prostaglandins. Studies in vitro have demonstrated a linkage between the pathways involved in the production of ROS and pro-inflammatory mediators. These studies support the notion that agents capable of inhibiting both oxidative stress and inflammation pathways would be particularly useful in the modulation of inflammation.

Treatment of Inflammation in Joint Tissues Using Drugs

The central role of COX-2 and $PGE_2$ in the pathophysiology of osteoarthritis is reflected in the widespread use of selective COX-2 inhibitors and a variety of non-selective non-steroidal anti-inflammatory drugs (NSAIDs) for the treatment of the disorder. However, prolonged administration of these drugs has adverse side effects, including gastrointestinal pathologies and disruption of cartilage proteoglycan metabolism. Studies in human and animal models have demonstrated impaired bone healing and repair with the use of COX inhibitors. Therefore, there is a need for alternative treatments for the management of inflammation that do not center on the use of NSAIDs to inhibit the production of $PGE_2$ and other pro-inflammatory mediators.

Treatment of Inflammation in Joint Tissues Using Nutraceuticals

Avocado/Soybean Unsaponifiables (ASU)

Many studies have documented the benefits of avocado/soybean unsaponifiables (ASU) for promoting joint health and the management of osteoarthritis. Clinical studies have reported beneficial effects of ASU in human and equine osteoarthritis patients as well as in experimental animal models of OA. The mechanisms that could account for the beneficial effects of ASU for osteoarthritis have been studied in vitro using bovine and human joint tissue cells. These studies showed that ASU inhibits the expression and production of cytokines, chemokines, $PGE_2$, nitric oxide, and MMPs. ASU also exerts anabolic effects on cartilage metabolism by enhancing synthesis of cartilage matrix components while suppressing their degradation.

Earlier studies using human osteoarthritic chondrocyte cultures found that ASU significantly reduces the stimulating effect of IL-1β on $PGE_2$ production. Of the two isoforms of cyclooxygenases involved in prostaglandin synthesis, COX-2 is highly inducible in response to cytokine exposure. High levels of COX-2 expression have been demonstrated in human synovial tissue). Several studies in experimental animals and humans have shown that $PGE_2$ synthesis and COX-2 expression are upregulated in synovial membranes in OA. Increased levels of $PGE_2$ have been detected in synovial tissue and in synovial fibroblasts in OA. There is experimental evidence that synovial tissue is the major source of eicosanoids found in osteoarthritic synovial fluid. Cytokines IL-1β and TNF-α enhance synoviocyte production of $PGE_2$. The reported decrease in $PGE_2$ synthesis by ASU appears to be associated with a decrease in COX-2 gene expression.

Lipoic Acid (LA)

Lipoic acid (LA), also known as 1,2 dithiolane-3-pentanoic acid, 1,2-dithiolane-3-valeric acid, or 6,8-thioctic acid, is a potent, naturally occurring, low molecular weight antioxidant. Lipoic acid is synthesized enzymatically in the mitochondrion from octanoic acid. It is a critical cofactor of mitochondrial decarboxylation reactions and is essential for adequate ATP production. Lipoic acid exists in enantiomeric forms: R-lipoic acid (R-LA) and S-lipoic acid (S-LA). In biological systems, only R-LA is conjugated to lysine residues in the amide linkage. The oxidized (LA) and reduced (DHLA) forms represent a potent redox couple. The biological effect of LA include scavenging of reactive oxygen species, regeneration of endogenous antioxidants such as glutathione and vitamin E, metal ion chelating, and repair oxidative damage in macromolecules. Both LA and DHLA are capable of scavenging reactive oxygen species (ROS) and reactive nitrogen species (RNS), and have the ability to prevent protein carbonyl formation. LA and DHLA can regenerate other endogenous antioxidants such as vitamin C, vitamin E, and glutathione, thereby protecting cells against oxidative stress. Recent evidence suggests that LA not only acts as a true oxidant scavenger but in addition acts as an activator of cellular stress response pathways.

Studies indicate that orally administered LA elicits biological activities critical in the defense against oxidative stress related insults. There is a growing body of evidence suggesting that orally administered LA is bioavailable, safe in moderate doses and elicits several metabolic and clinical effects. Reported clinical benefits of LA involve the following disorders: diabetic polyneuropathies (Ametov et al. The sensory symptoms of diabetic polyneuropathy are improved with alpha-lipoic acid: the SYDNEY trial. *Diabetes Care.* 2003, 26:770-776, disorders affecting the vascular system such as hypertension, inflammation associated diseases such as coronary atherosclerosis, and cognition-neurological disorders such as Alzheimer's Disease (Hager et al., Alpha-lipoic acid as a new treatment option for Azheimer type dementia, *Archives of Gerontology and Geriatrics,* 2001, 32:275-282 and Hager et al., Alpha-lipoic acid as a new treatment option for Alzheimer's disease—a 48 months follow-up analysis *J Neural Transm Suppl.* 2007, 72:189-93. However, little is known about the role of LA in joint inflammation. The effect of LA at the cellular level is diverse and its mode of action involves biologic activities such as anti-oxidation, anti-inflammation, anti-chelation and enhancement of kinases and phosphatases.

Derivatives of lipoic acid have been described in the art. Some derivatives of lipoic acid provide improved biological activity, improved pharmacokinetic properties such as longer half lives, improved bioavailability, and decreased drug interaction profiles. Derivatives of lipoic acid have been described in the following publications, hereby incorporated by reference: Gruzman et al. Synthesis and characterization of new and potent alpha-lipoic acid derivatives. *Bioorganic & Medicinal Chemistry,* 2004, 12:1183-1190; Melagraki et al. Synthesis and evaluation of the antioxidant and anti-inflammatory activity of novel coumarin-3-aminoamides and their alpha-lipoic acid adducts. *European Journal of Medicinal Chemistry,* 2009, 44:3020-3026; Gurkan et al., Syntheses of novel indole lipoic acid derivatives and their antioxidant effects on lipid peroxidation. *Archiv der Pharmazie,* 2005, 338:67-73; Ortial et al., Fluorinated amphiphilic amino acid derivatives as antioxidant carriers: a new class of protective agents. *J Med Chem* 2006; 12-2820; and Koufaki et al. Sign and synthesis of antioxidant alpha-lipoic acid hybrids. *Methods Mol Biol,* 2010, 594:297-309.

SUMMARY OF THE INVENTION

The present invention provides an orally administrable composition comprising: (i) avocado/soybean unsaponifiables (ASU) and (ii) lipoic acid or derivatives thereof. Other forms of administration, such as topical, rectal and sublingual may also be used with this composition.

The present invention also provides a method of preventing, treating, protecting, repairing or reducing damage to connective tissues or reducing symptoms associated with damage to connective tissue in an avian or mammalian subject, comprising administering to the subject: (i) avocado/soybean unsaponifiables and (ii) lipoic acid, or derivatives thereof.

The present invention additionally provides a method of reducing levels of one or more inflammatory mediators in connective tissue, comprising administering to a mammalian subject: (i) avocado/soybean unsaponifiables and (ii) lipoic acid or derivatives thereof.

Other novel features and advantages of the present invention will become apparent to those skilled in the art upon examination of the following or upon learning by practice of the invention.

DETAILED DESCRIPTION OF THE INVENTION

The present invention provides for methods comprising administration of (i) avocado/soybean unsaponifiables (ASU), and (ii) lipoic acid or derivatives thereof, to a mammalian subject. The avocado/soybean unsaponifiables (ASU) and lipoic acid or derivatives thereof may be administered together in one composition or dosage form, or they may be administered separately. In preferred embodiments, the avocado/soybean unsaponifiables (ASU) and lipoic acid or derivatives thereof, are administered together in one composition or dosage form, or separately, within a period in which their therapeutic properties overlap, preferably within 1 hour, more preferably within 30 minutes, and most preferably within 5 minutes.

The term "mammalian subject" is any mammal, including, but not limited to humans, dogs, cats, horses, cows, and camels. The term "avian subject" refers to birds.

The term "avocado/soybean unsaponifiables (ASU)" refers to a mixture of avocado unsaponifiables and soybean unsaponifiables. "Unsaponifiables" are compounds which do not react with alkali to form a soap. The term "avocado unsaponifiables" refers to an extract of compounds obtained from any part of an avocado (genus *Persea*). The avocado may be any species of avocado, such as but not limited to *Persea americana* and *Persea schiedeana* The term "soybean unsaponifiables" refers to an extract of compounds obtained from any part of a soybean (*Glycine max*). The soybean may be any species of soybean, such as but not limited to Glycine wild Avocado/soybean unsaponifiables are well known in the art and are described in numerous patents and publications, including but not limited to: U.S. Pat. Nos. 6,797,289, 7,449, 487, and 6,759,543; U.S. Patent Application Publication Nos. 20080176935 and 20090087503; Their, "Unsaponifiable constituents of avocado and soya oils. Treatment of certain forms of arthralgia," *J. Med. Lyon* 53 (222): 195-8 (February 1972); Trevoux, "Unsaponifiable fractions of the avocado and soybean in gynecology,"*J. Gynecol. Obstet. Biol. Reprod.* 6 (1): 99-105 (January 1977); Lamaud et al., "Biochemical modifications of connective tissue induced by the non-saponifiables of avocado and soy-bean oils administered percutaneously in the hairless rat," *Pathol. Biol.* 26 (5): 269-74 (May-June 1978); Boumediene et al., "Avocado/soya unsaponifiables enhance the expression of transforming growth factor beta 1 and beta 2 in cultured articular chondrocytes," *Arthritis Rheum.* 42 (1): 148-56 (January 1999); Henrotin et al., "Effects of three avocado/soybean unsaponifiable mixtures on metalloproteinases, cytokines and prostaglandin E2 production by human articular chondrocytes," *Clin. Rheumatol.* 17 (1): 31-9 (1998); Maheu et al. "Symptomatic efficacy of avocado/soybean unsaponifiables in the treatment of osteoarthritis," *Arthritis Rheum.* 41 (1): 81-91 (January 1998); and Blotman et al., "Efficacy and safety of avocado/soybean unsaponifiables in the treatment of symptomatic osteoarthritis," *Rev. Rheum. Engl. Ed.* 64 (12): 825-34 (December 1997), which are each incorporated by reference in their entirety. In addition, avocado/soybean unsaponifiables in combination with another ingredient (glucosamine) are currently marketed in the United States under the trade name AVOCA ASU®. Avocado/soybean unsaponifiables are also marketed in Europe under the trade name PIASCLEDINE®. Dosage calculations can be determined by those of skilled in the art by evaluating body weight, surface area and species differences. The typical daily dosage of avocado/soybean unsaponifiables (ASU) is about 1 mg/kg to about 12 mg/kg, preferably about 2 mg/kg to about 5 mg/kg, and more preferably about 3 mg/kg to about 4 mg/kg. In some embodiments, the typical daily dosage is at least 5 mg for small animals, and up to 12 g for large animals. The daily dosage refers to the total dosage administered in a 24-hour period.

In some embodiments, the avocado/soybean unsaponifiables are administered on a daily basis. In other embodiments, the avocado/soybean unsaponifiables are administered less frequently, such as once every other day or once a week or once a month. In some embodiments, the avocado/soybean unsaponifiables are administered at a daily dose of about 1 mg/kg to about 12 mg/kg, preferably about 2 mg/kg to about 5 mg/kg, and most preferably about 3 mg/kg to about 4 mg/kg for three days to one month, preferably for about one week, then the daily dose is decreased to about 25% to about 90% of the initial dose, preferably about 50% to about 80% of the initial dose, and most preferably about 60% to about 75% of the initial dose. Dosage calculations can be determined by those skilled in the art by evaluating body weight, surface area & species differences.

The avocado/soybean unsaponifiables may be administered at a frequency of one time per week to five times daily, preferably once every two days to three times daily, more preferably one to two times daily. In preferred embodiments, the avocado/soybean unsaponifiables are administered once daily. The avocado/soybean unsaponifiables may be taken with or without the administration of food.

The term "lipoic acid or derivates thereof" refers to a compound having the following structure:

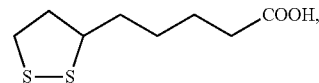 [SMILES: O=C(O)CCCCC1CCSS1]

and salts or derivatives thereof. Lipoic acid is also known as α-lipoic acid; thioctic acid; 6,8-dithiooctanoic acid; and 1,2-dithiolane-3-valeric acid. Derivatives of lipoic acid include but is not limited to esters and amides of lipoic acid, conjugates of lipoic acid, and analogues of lipoic acid. Esters and amides of lipoic acid include but are not limited to 5-[1,2]-dithiolan-3-yl-pentanoic acid 3-(5-[1,2]-dithiolan-3-yl-pentanoyloxy)-propyl ester and 51',2'-dithiolan-3-yl-pentanoic acid 3-(5-[1,2]-dithiolan-3-yl-pentanoylamino)-propyl-amide. Conjugates of lipoic acid include but are not limited to coumarin-lipoic acid conjugates; indole-α-lipoic acid conjugataes such as 5-[1,2]dithiolan-3-yl-pentanoic acid [1-(4-fluoro-benzyl)-1H-indole-5-yl]-amide; and amphiphilic lipoic acid derivatives such N-lactobionyl-N$^\varepsilon$-(5-[1,2]-dithiolan-3-yl-penoyl)-L-lysinyl-1H,1H,2H-perfluorooctyla-mide. Analogues of lipoic acid include but are not limited to 1,2-diselenolane-3-pentanoic acid and 1,2-dithiolane derivatives of lipoic acid containing catechol moieties linked through heteroaromatic rings. Derivatives of lipoic acid have been described in the following publications, hereby incorporated by reference: Gruzman et al. Synthesis and characterization of new and potent alpha-lipoic acid derivatives, *Bioorganic & Medicinal Chemistry,* 2004, 12:1183-1190; Melagraki et al. Synthesis and evaluation of the antioxidant and anti-inflammatory activity of novel coumarin-3-aminoamides and their alpha-lipoic acid adducts. *European Journal of Medicinal Chemistry,* 2009, 44:3020-3026; Gurkan et al., Syntheses of novel indole lipoic acid derivatives and their antioxidant effects on lipid peroxidation. *Archiv der Pharmazie,* 2005, 338:67-73; Ortial et al., Fluorinated amphiphilic amino acid derivatives as antioxidant carriers: a new class of protective agents. *J Med Chem* 2006; 12-2820; Koufaki et al. Sign and synthesis of antioxidant alpha-lipoic acid hybrids. *Methods Mol Biol,* 2010, 594:297-309; Sen et al., A positively charged alpha-lipoic acid analogue with increased cellular uptake and more potent immunomodulatory activity. *Bio-* chem Biophys Res Commun, 1998, 247:223-228; Harnett et al., Novel lipoic acid analogues that inhibit nitric oxide synthase. *Bioorg Med Chem Lett,* 2002, 12:1439-1442; and Acker, Syntheses of Reduced Lipoic Acid and Analogs of Lipoic Acid, *Journal of Organic Chemistry,* 1963, 28:2533-2536. The lipoic acid and derivatives thereof may comprise racemates, enantiomers, or mixtures thereof.

The typical daily dosage of lipoic acid or a derivative of lipoic acid can range from about 1 mg/day to about 15,000 mg/day. The typical daily dosage of lipoic acid or derivatives of lipoic acid can range from about 0.25 mg/kg/day to about 50 mg/kg/day. The daily dosage of lipoic acid refers to the total amount of lipoic acid administered in a 24-hour period. The daily dosage can be provided in one or more administrations. For example, the daily dosage can be administered once daily, twice daily, or three or more times daily. In preferred embodiments, the daily dosage is administered in one to five administrations, preferably one to three administrations, and more preferably one or two administrations in a 24-hour period. The daily dosage may vary according to the type of subject. For example, in humans, the daily dosage is preferably about 25 to about 2,000 mg/day, more preferably about 50 to about 1,500 mg/day, and most preferably about 100 to about 1200 mg/day, or preferably about 0.5 to about 50 mg/kg/day, more preferably about 0.6 to about 40 mg/kg/day, and most preferably about 1.25 to about 30 mg/kg/day. In dogs, the daily dosage is preferably about 1 to about 1,500 mg/day, more preferably about 10 to about 750 mg/day, and most preferably about 20 to about 600 mg/day, or preferably about 1 to about 100 mg/kg/day, more preferably about 10 to about 60 mg/kg/day, and most preferably about 20 mg/kg/day. In cats, the daily dosage is preferably about 1 to about 100 mg/day, more preferably about 3 to about 50 mg/day, and most preferably about 3 to about 15 mg/day, or preferably about 0.5 to about 25 mg/kg/day, more preferably about 1 to about 20 mg/kg/day, and most preferably about 3 to 15 mg/kg/day. In horses, the daily dosage is preferably about 125 to about 15,000 mg/day, more preferably about 500 to about 12,500 mg/day, and most preferably about 200 to about 10,000 mg/day, or preferably about 0.5 to about 100 mg/kg/day, more preferably about 1 to about 50 mg/kg/day, and most preferably about 1 to 25 mg/kg/day.

In some preferred embodiments, the lipoic acid or derivatives, analogues, racemates, or enantiomers of lipoic acid, or mixtures thereof, are administered for three days to one month, preferably for about one week, then the daily dose is decreased down to 75% of the initial dose. Dosage calculations can be determined by those skilled in the art by evaluating body weight, surface area & species differences.

The lipoic acid or derivatives thereof may be administered at a frequency of one time per week to five times daily, preferably once every two days to three times daily, more preferably one to two times daily. In preferred embodiments, the lipoic acid or derivatives thereof are administered once daily. The lipoic acid or derivatives thereof may be taken with or without the administration of food.

In some embodiments, the combination of (i) avocado/soybean unsaponifiables and (ii) lipoic acid or derivatives thereof demonstrate synergy. Synergy refers to the effect wherein a combination of two or more components provides a result which is greater than the sum of the effects produced by the agents when used alone. In preferred embodiments, the result is statistically significant and greater than the additive effect. In some embodiments, the combination of avocado/soybean unsaponifiables and lipoic acid or derivatives thereof have a statistically significant, greater effect than each component alone. In preferred embodiments, the combination of avocado/soybean unsaponifiables and lipoic acid or derivatives thereof demonstrate synergy in one or more of the following: preventing, treating, repairing or reducing damage to connective tissues; reducing symptoms associated with damage to connective tissue in an avian or mammalian subject; and reducing levels of one or more inflammatory mediators in connective tissue.

The present invention provides a method of preventing, treating, repairing, reducing damage, or controlling inflammation of connective tissues, protecting cartilage, or reducing symptoms associated with damage to connective tissue in an avian or mammalian or avian subject, comprising administering to the subject: (i) avocado/soybean unsaponifiables and (ii) lipoic acid or derivatives thereof. The term "connective tissue" includes but not limited to cartilage, bone, synovium, ligament, meniscus, and tendon. In some embodiments, the administration of avocado/soybean unsaponifiables and (ii) lipoic acid or derivatives thereof may prevent, treat, repair or reduce damage to connective tissues. The damage to connective tissue may be a result of physical injury or may represent "wear and tear" from continual use, weight and age, for example, from osteoarthritis. Damage to connective tissue may also result from disease such as rheumatoid arthritis, synovial disorders, infection related rheumatic diseases and inflammatory connective tissue disorders. In some embodiments, the administration of avocado/soybean unsaponifiables and (ii) lipoic acid or derivatives thereof may reduce symptoms associated with damage to connective tissue in an avian or mammalian subject. Symptoms associated with damage to connective tissue include, but are not limited to: pain, discomfort, pressure, inflammation, stiffness and/or swelling.

The present invention also provides a method of reducing levels of one or more inflammatory mediators in connective tissue, comprising administering to an avian or mammalian subject: (i) avocado/soybean unsaponifiables and (ii) lipoic acid or derivatives thereof. The inflammatory mediators include, but are not limited to prostaglandins such as prostaglandin $E_2$ ($PGE_2$), cytokines such as interleukin-1β (IL-1β) and tumor necrosis factor-α (TNF-α), chemokines, leukotrienes, nitric oxide, and reactive oxygen species.

The administration of avocado/soybean unsaponifiables and lipoic acid, or derivatives thereof may also be useful for treating, preventing, and reducing damage or reducing symptoms associated with conditions affecting the cardiovascular system, nervous system, musculoskeletal system and gastrointestinal system. The present invention also provides for an orally administrable composition comprising: (i) avocado/soybean unsaponifiables and (ii) lipoic acid or derivatives thereof. The orally administrable composition is any dosage form which can be administered orally, such as, but not limited to: a capsule, a tablet, a powder that can be dispersed in a beverage, a liquid such as a solution, suspension, or emulsion, a soft gel/chew capsule, a chewable bar or other convenient dosage form such as oral liquid in a capsule, as known in the art.

The orally administrable composition may contain one or more non-active pharmaceutical ingredients (also known generally herein as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. The excipients are preferably pharmaceutically acceptable excipients. Examples of classes of pharmaceutically acceptable excipients include lubricants, buffering agents, stabilizers, blowing agents, pigments, coloring agents, flavoring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof.

The orally administrable compositions may further comprise one or more active ingredients. For example, the compositions may further comprise one or more drugs or nutritional supplements. In some embodiments, the compositions may further comprise compounds which are beneficial to connective tissue. Example include, but are not limited to glycosaminoglycans such as chondroitin, aminosugars such as glucosamine, methylsulfonylmethane (MSM), green tea extracts, boswellia extracts, *scutellaria* extracts, acacia extracts, turmeric extracts, curcumin, cetyl myristoleate complex (CMO) and egg shell membrane.

All references cited herein are incorporated by reference in their entirety.

EXAMPLES

Example 1

Effect of Avocado/Soybean Unsaponifiables (ASU) and Lipoic Acid (LA) on Prostaglandin $E_2$ ($PGE_2$) Production in Lipopolysaccharide (LPS) Activated Equine Chondrocyte Cultures Chondrocytes were pre-treated with avocado/soybean unsaponifiables (ASU) at a concentration of 8.3 µg/ml and different concentrations of lipoic acid (LA) for 24 hrs, then activated with lipopolysaccharide (LPS) (1 ng/ml). Lipopolysaccharide (LPS) is an endotoxin derived from the bacterial cell wall which is used as a broad inflammatory stimulus to induce prostaglandin $E_2$ ($PGE_2$) production. After an additional 24 hrs, supernatant was collected and assayed for $PGE_2$ levels. Statistical significance between the activated control and the pre-treated groups were analyzed using Tukey post-hoc analysis (mean±1 SD, n=3).

The combination of avocado/soybean unsaponifiables (ASU) at a concentration of 8.3 µg/ml and lipoic acid (LA) at concentrations of 2.5, 1.25 and 0.625 µg/ml reduced $PGE_2$ levels significantly more than either ASU (<0.001) or LA (p<0.001) alone. The results are graphed in FIG. 1.

Example 2

Effect of ASU and Lipoic Acid (LA) on Prostaglandin $E_2$ ($PGE_2$) Production in Hydrogen Peroxide ($H_2O_2$) Activated Equine Chondrocyte Cultures Chondrocytes were pre-treated with avocado/soybean unsaponifiables (ASU) at a concentration of 8.3 µg/ml and different concentrations of lipoic acid (LA) for 24 hrs, then activated with hydrogen peroxide (500 µM). Hydrogen peroxide is a potent oxidant used to induce prostaglandin $E_2$ ($PGE_2$) production. After an additional 24 hrs, supernatant was collected and assayed for $PGE_2$ levels. Statistical significance between the activated control and the pre-treated groups were analyzed using Tukey post-hoc analysis (mean±1 SD, n=3). The combination of avocado/soybean unsaponifiables (ASU) at a concentration of 8.3 µg/ml and lipoic acid (LA) at concentrations of 2.5 and 1.25 µg/ml reduced $PGE_2$ levels significantly more than either ASU (<0.001) or LA (p<0.05) alone. The results are graphed in FIG. 2.

What is claimed is:

1. An oral composition for treating and reducing damage to connective tissue and reducing levels of one or more inflammatory mediators in connective tissue comprising an effective amount of:
   (i) avocado/soybean unsaponifiables; and
   (ii) lipoic acid, wherein the ratio of avocado/soybean unsaponifiables: lipoic acid is 3:1 to 13:1 w/v.

* * * * *